(12) United States Patent
Fujimoto et al.

(10) Patent No.: US 7,816,837 B2
(45) Date of Patent: Oct. 19, 2010

(54) SURFACE ACOUSTIC WAVE SENSOR

(75) Inventors: Koji Fujimoto, Otsu (JP); Michio Kadota, Kyoto (JP); Yoshiharu Yoshii, Kanazawa (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 1112 days.

(21) Appl. No.: 10/561,251

(22) PCT Filed: Apr. 8, 2004

(86) PCT No.: PCT/JP2004/005077

§ 371 (c)(1),
(2), (4) Date: Dec. 19, 2005

(87) PCT Pub. No.: WO2005/003752

PCT Pub. Date: Jan. 13, 2005

(65) Prior Publication Data

US 2007/0107516 A1    May 17, 2007

(30) Foreign Application Priority Data

Jul. 4, 2003    (JP) .............................. 2003-191759

(51) Int. Cl.
*H02N 2/00*    (2006.01)
(52) U.S. Cl. .............................. 310/313 D; 310/313 R; 310/313 B; 422/88; 73/19.03; 73/24.01; 73/31.06
(58) Field of Classification Search ... 310/313 A–313 D
See application file for complete search history.

(56) References Cited

U.S. PATENT DOCUMENTS 5,283,037 A * 2/1994 Baer et al. ............... 422/82.01

(Continued)

FOREIGN PATENT DOCUMENTS

JP    02-238357    9/1990

(Continued)

OTHER PUBLICATIONS

Springer et al., Wireless identification and sensing using surface acoustic wave devices, 1999, Elsevier Science Ltd., Mechatronics 9 (1999), p. 745-756.*

(Continued)

*Primary Examiner*—Tony G Soohoo
*Assistant Examiner*—Robert Eom
(74) *Attorney, Agent, or Firm*—Keating & Bennett, LLP

(57) ABSTRACT

A surface acoustic wave sensor for detecting a target substance by measuring the change in frequency due to the mass applied to a reaction membrane placed on a surface acoustic wave element having high sensitivity due to the improvement of the surface acoustic wave element structure. The surface acoustic wave sensor includes an SH-type surface acoustic wave and a rotated Y-cut $LiTaO_3$ substrate having Euler angles (0°, 120° to 140°, 0°±5°); electrodes principally containing Au, for exciting a surface acoustic wave, the electrodes being arranged on the $LiTaO_3$ substrate; and a reaction membrane bound to a target substance or a binding substance bound to the target substance covering the electrodes arranged on the $LiTaO_3$ substrate. The interdigital transducers have a normalized thickness of about 3.0% to about 5.0%, the normalized thickness being determined by normalizing the thickness of the interdigital transducers by the wavelength of the surface acoustic wave.

5 Claims, 6 Drawing Sheets

U.S. PATENT DOCUMENTS

| | | | |
|---|---|---|---|
| 5,418,058 A | * | 5/1995 | Li et al. .................. 428/327 |
| 5,910,286 A | * | 6/1999 | Lipskier .................. 422/68.1 |
| 6,366,002 B1 | | 4/2002 | Kadota |
| 6,369,667 B1 | | 4/2002 | Kadota et al. |

FOREIGN PATENT DOCUMENTS

| | | |
|---|---|---|
| JP | 06-133759 | 5/1994 |
| JP | 7-198428 A | 8/1995 |
| JP | 10-090270 | 4/1998 |
| JP | 2000-323956 | 11/2000 |
| JP | 2001-077662 | 3/2001 |

OTHER PUBLICATIONS

Stubbs et al., "Cocaine Detection Using Suarface Acoustic Wave Immunoassay Sensors," IEEE International Frequency Control Symposium and PDA Exhibition, Oct. 31, 2002, pp. 289-293.

Barie et al., "The Use of Dextran as an Intermediate Layer: A New Approach Towards SAW Baed Biosensors," 1999 Joint Meeting EFTF-IEEE IFCS, May 19, 2000, vol. 2, pp. 997-1000.

Kondoh et al., "SH-SAW Biosensor Based on pH Change," 1993 IEEE Ultrasonic Symposium, Jul. 14, 1994, vol. 1, pp. 337-340.

Shiokawa et al., "Fundamental and Application of SAW Sensor", Dai 32 Kai EM Symposium, May 15, 2003, pp. 77-84.

International Search Report for PCT Application No. PCT/JP2004/005077; mailed Jul. 27, 2004.

Official communication issued in counterpart Japanese Application No. 2005-511304, mailed on Oct. 28, 2008.

Furukawa et al.: "Characteristics of Leaky SAW Propagating Along Liquid/LiNbO$_3$/Sapphire Structure and Its Application to Liquid Sensor," 1997 IEEE Ultrasonics Symposium; 1997; vol. 1; pp. 433-436.

* cited by examiner

SURFACE ACOUSTIC WAVE SENSOR

BACKGROUND OF THE INVENTION

1. Field of the Invention

The present invention relates to surface acoustic wave sensors such as biosensors and gas sensors. The present invention particularly relates to a surface acoustic wave sensor, using an SH-type surface acoustic wave, for detecting a target substance on the basis of a change in frequency due to the mass applied to the sensor.

2. Description of the Related Art

Various surface acoustic wave sensors including surface acoustic wave elements have been used to detect various substances. For example, a surface acoustic wave sensor for detecting biological substances such as DNAs and antibodies includes a reaction membrane, placed on a surface acoustic wave element, reacting only with a specific biological substance such as a DNA or an antibody. Such a DNA or antibody is bound to the reaction membrane by reaction. As a result, a mass is applied to the surface acoustic wave element. The presence or content of the DNA or the antibody is detected on the basis of the change in frequency due to the applied mass.

Japanese Unexamined Patent Application Publication No. 10-90270 discloses an example of this type of surface acoustic wave sensor. The surface acoustic wave sensor disclosed in this known document can detect 2-MIB (2-methylisoborneol) that is an earthy-smelling substance contained in water. With reference to FIG. 12, the surface acoustic wave sensor 101 includes interdigital transducers 103 and 104, a metal thin-film 105, and a piezoelectric substrate 102 on which the interdigital transducers 103 and 104 and the metal thin-film 105 are arranged. Amplifiers 106 and 107 are placed between one pair of the interdigital transducers 103 and the other pair of the interdigital transducers 104 and connected thereto. A mixer 108 is connected to rear portions of the interdigital transducers 104 for output and rear portions of the amplifiers 106 and 107. An output from the surface acoustic wave sensor 101 is extracted from the mixer 108.

In the surface acoustic wave sensor 101, a camphor-Ova complex is immobilized on the upper surface of the piezoelectric substrate 102. The camphor-Ova complex functions as a reaction membrane. As a result, 2-MIB is detected by the reaction between the camphor-Ova complex and 2-MIB.

That is, a complex antigen containing protein and camphor having a structure similar to that of 2-MIB, which is an earthy-smelling substance, is immobilized on the surface acoustic wave sensor 101. The surface acoustic wave sensor 101 is immersed in a test solution containing a certain amount of a 2-MIB antibody specifically bound to 2-MIB and the camphor-protein complex antigen competitively reacts with 2-MIB which is present in the solution and of which the content is unknown. The amount of the 2-MIB antibody bound to the camphor-protein complex antigen immobilized on the surface acoustic wave sensor 101 is determined from the change in output due to the mass applied to the surface acoustic wave sensor. The content of 2-MIB in the test solution is determined from the difference between the amount of the 2-MIB antibody bound to the camphor-protein complex antigen in the presence of 2-MIB and the amount of that in the absence of 2-MIB.

As described above, surface acoustic wave sensors have been widely used to detect or determine biological substances such as DNAs, antigens, and antibodies and various substances such as 2-MIB, which is a cause of earthy odor. This type of surface acoustic wave sensor includes a piezoelectric substrate and a reaction membrane, placed thereon, which is suitable for a target substance. The target substance is detected or determined from the change in frequency due to the mass applied to the reaction membrane.

In the surface acoustic wave sensor, the change in mass is detected as the change in frequency. Therefore, an increase in frequency change leads to an increase in the sensitivity of the surface acoustic wave sensor. In order to enhance the sensitivity, reaction membranes suitable for target substances have been widely investigated.

On the other hand, the relationship between the sensitivity of the surface acoustic wave sensor and the structure of a surface acoustic wave element included in the surface acoustic wave sensor has not been intensively investigated.

SUMMARY OF THE INVENTION

In order to overcome the problems described above, preferred embodiments of the present invention provide a surface acoustic wave sensor which includes a surface acoustic wave element with an improved structure and which therefore has high sensitivity. The surface acoustic wave sensor further includes a reaction membrane placed on the surface acoustic wave element and detects a target substance from the change in the mass applied to the surface acoustic wave element.

According to a preferred embodiment of the present invention, a surface acoustic wave sensor for detecting a minute mass applied to a surface acoustic wave element on the basis of the change in frequency using an SH-type surface acoustic wave includes a rotated Y-cut $LiTaO_3$ substrate having Euler angles (0°, 0° to 18°, 0°±5°) or (0°, 58° to 180°, 0°±5°); electrodes, principally containing Au, for exciting a surface acoustic wave, the electrodes being arranged on the $LiTaO_3$ substrate, and a reaction membrane, bound to a target substance or a binding substance bound to the target substance, covering the electrodes arranged on the $LiTaO_3$ substrate. The electrodes have a normalized thickness of about 0.8% to about 9.5%, the normalized thickness being determined by normalizing the thickness of the electrodes by the wavelength of the surface acoustic wave.

The rotated Y-cut $LiTaO_3$ substrate preferably has Euler angles (0°, 120° to 140°, 0°±5°).

In a specific preferred embodiment of the present invention, the surface acoustic wave sensor further includes a bonding layer, placed between the reaction membrane and the electrodes, for enhancing the bond between the reaction membrane and the electrodes.

In another specific preferred embodiment of the present invention, the surface acoustic wave sensor further includes a protective layer, placed between the reaction membrane and the electrodes, lying over the electrodes and regions outside the electrodes.

In another specific aspect preferred embodiment of the present invention, the surface acoustic wave sensor further includes a protective layer, placed between the bonding layer and the electrodes, lying over the electrodes and regions outside the electrodes.

In another specific preferred embodiment of the present invention, the electrodes have a normalized thickness of about 1.2% to about 8.5%, the normalized thickness being determined by normalizing the thickness of the electrodes by the wavelength of the surface acoustic wave.

In another specific preferred embodiment of the present invention, the electrodes have a normalized thickness of about 1.9% to about 6.6%, the normalized thickness being determined by normalizing the thickness of the electrodes by the wavelength of the surface acoustic wave.

In another specific preferred embodiment of the present invention, the electrodes have a normalized thickness of about 3.0% to about 5.0%, the normalized thickness being determined by normalizing the thickness of the electrodes by the wavelength of the surface acoustic wave.

A biosensor according to a preferred embodiment of the present invention includes the surface acoustic wave sensor. The reaction membrane includes a substance bound to a biological substance that is a target substance and the mass applied to a surface of the substrate of the surface acoustic wave sensor is varied due to the bind of the biological substance to the reaction membrane.

Other features, elements, characteristics and advantages of preferred embodiments of the present invention will become more apparent from the following detailed description of the present invention.

BRIEF DESCRIPTION OF THE DRAWINGS

FIGS. 1A to 1D are illustrations showing the measurement principle of a surface acoustic wave sensor according to a preferred embodiment of the present invention, wherein FIG. 1A is a schematic front sectional view of the surface acoustic wave sensor immersed in a liquid containing no target substance, FIG. 1B is an illustration showing the change in frequency measured in the liquid containing no target substance, FIG. 1C is a schematic front sectional view of the surface acoustic wave sensor immersed in a liquid containing a target substance, and FIG. 1D is an illustration showing the change in frequency measured in the liquid containing the target substance.

DETAILED DESCRIPTION OF PREFERRED EMBODIMENTS

Preferred embodiments of the present invention will now be described in detail with reference to the accompanying drawings. Features of the present invention will become apparent from the description of preferred embodiments thereof.

Figure 1A:
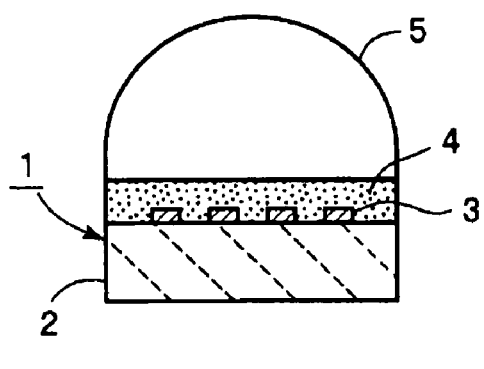
Figure 1C:
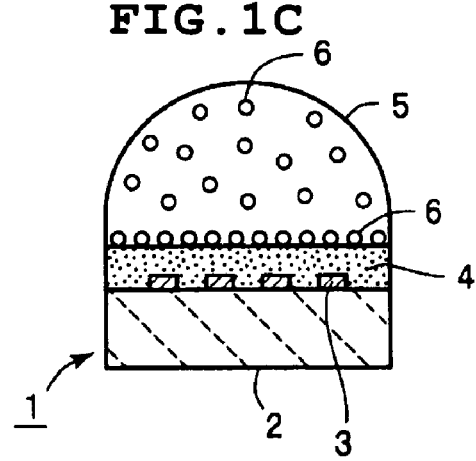
Figure 1B:
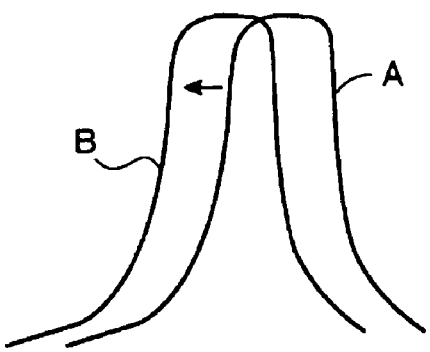
Figure 1D:
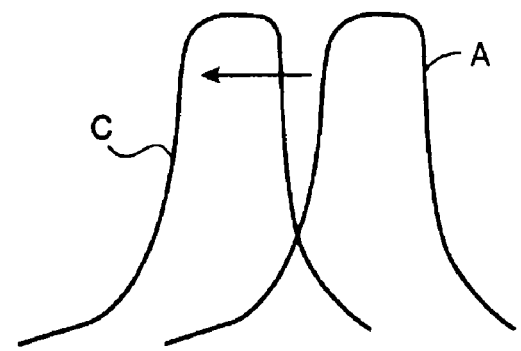
Figure 2:
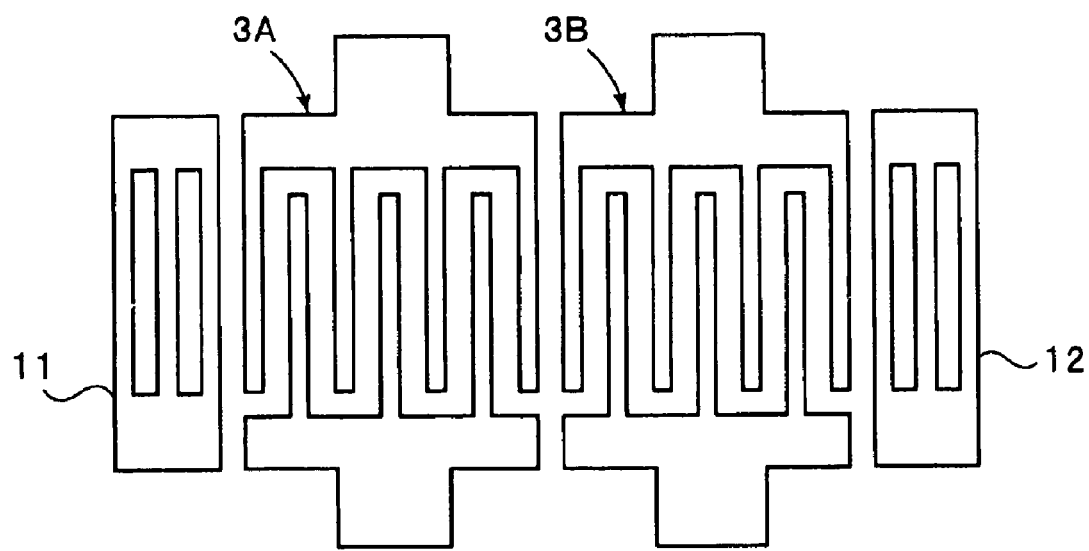
FIG. 2 is a schematic plan view showing the electrode structure of a two-port type surface acoustic wave resonator prepared in Experiment 1.

FIGS. 1A to 1B are illustrations showing the measurement principle of a surface acoustic wave sensor according to a preferred embodiment of the present invention.

The surface acoustic wave sensor 1 of the present preferred embodiment preferably includes an SH-type surface acoustic wave and includes a rotated Y-cut LiTaO$_3$ substrate 2 substrate having Euler angles (0°, 0° to 18°, 0°±5°) or (0°, 58° to 180°, 0°±5°). Interdigital transducers 3 for exciting the surface acoustic wave are arranged on the LiTaO$_3$ substrate 2. The interdigital transducers 3 are made of Au. The interdigital transducers 3 preferably have a normalized thickness of about 0.8% to about 9.5%, the normalized thickness being determined by normalizing the thickness of the interdigital transducers 3 by the wavelength of the surface acoustic wave.

A reaction membrane 4 is placed on the LiTaO$_3$ substrate 2. The reaction membrane 4 may be made of a material bound to a target substance or a binding substance bound to such a target substance.

When the surface acoustic wave sensor 1 is immersed in a liquid 5 containing no target substance, the liquid 5 contacts the reaction membrane 4 as shown in FIG. 1A. In this situation, although no target substance is present in the liquid 5, the liquid 5 contacts the reaction membrane 4. As a result, a mass is applied to a surface of the LiTaO$_3$ substrate 2 on which the interdigital transducers 3 are arranged. Therefore, as shown in FIG. 1B, the frequency response A of the surface acoustic wave sensor 1 free from the liquid 5 is shifted to the frequency response B of the surface acoustic wave sensor 1 immersed in the liquid 5, that is, the frequency is reduced. The reduction of the frequency is relatively small.

On the other hand, when the surface acoustic wave sensor 1 is immersed in the liquid 5 containing a target substance 6, the target substance 6 is bound to the reaction membrane 4 as shown in FIG. 1C. Therefore, the mass of the target substance 6 is applied to the substrate surface having the interdigital transducers 3 arranged thereon in addition to the effect of the liquid 5.

The target substance 6 contained in the liquid 5 reacts with the reaction membrane 4 and is bound to the reaction membrane 4. The SH-type surface acoustic wave excited on the LiTaO$_3$ substrate 2 is greatly affected by the mass of the target substance 6. Therefore, the presence of the target substance can be detected from the change in frequency as described above.

One of the unique features of the surface acoustic wave sensor 1 is that the surface acoustic wave sensor 1 uses the SH-type surface acoustic wave and includes the rotated Y-cut LiTaO$_3$ substrate 2 having the above-described Euler angles and the interdigital transducers 3 are made of Au and have a normalized thickness of about 0.8% to about 9.5%, the normalized thickness being determined by normalizing the thickness of the interdigital transducers 3 by the wavelength of the surface acoustic wave. As is clear from experiments below, the surface acoustic wave sensor 1 has high sensitivity due to the above configuration. This will now be described with reference to the experiments.

EXPERIMENT 1

Two-port type surface acoustic wave resonators were each prepared in such a manner that a 36°-rotated Y-cut LiTaO$_3$ substrate was prepared and an interdigital transducer and reflectors were formed on the LiTaO$_3$ substrate, the reflectors being arranged on both sides of the interdigital transducer in the direction of the propagation of a surface acoustic wave. The resonator had no reaction membrane.

Figure 3:
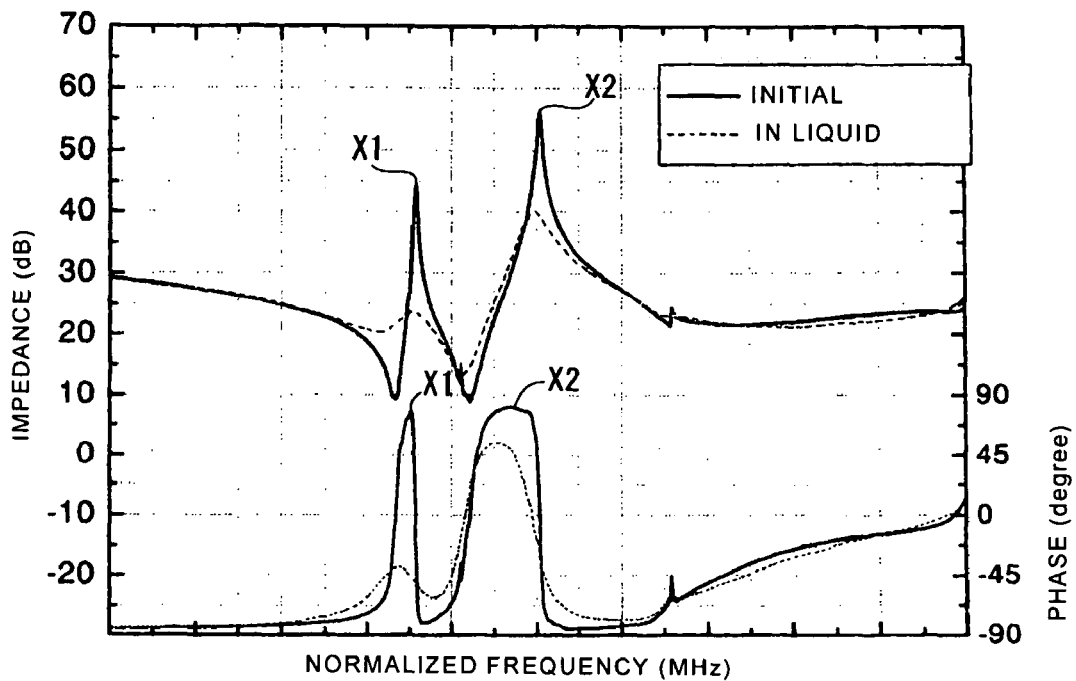
FIG. 3 is a graph showing the initial impedance-frequency response measured using a Rayleigh wave, that measured using an SH wave, and the impedance-frequency response after damping in liquid.

One of the surface acoustic wave sensors that included the following interdigital transducer was measured for frequency response: an interdigital transducer having a normalized thickness of about 2%, the normalized thickness being determined by normalizing the thickness of the electrodes by the wavelength of the surface acoustic wave. With reference to FIG. 3, the solid lines indicate the impedance-frequency response of the surface acoustic wave sensor in an initial state and the phase-frequency response thereof.

With reference to FIG. 3, Arrow X1 indicates resonances associated with a Rayleigh wave and Arrow X2 indicates resonances associated with an SH-type surface acoustic wave.

With reference to FIG. 3, the broken lines indicate the impedance-frequency response of the surface acoustic wave sensor immersed in ethanol and the phase-frequency response thereof. As is clear from the comparison between the responses indicated by the solid lines and those indicated by the broken lines, for the resonances X1 associated with the Rayleigh wave, the excitation in liquid is weak. However, for the resonances X2 associated with the SH-type surface acoustic wave, the excitation is not weak. That is, the Rayleigh wave is useless for the sensor immersed in liquid. Therefore, the surface acoustic wave sensor can function well using the SH-type surface acoustic wave even if the surface acoustic wave sensor is immersed in liquid.

Therefore, according to preferred embodiments of the present invention, the surface acoustic wave sensor uses the response of the SH-type surface acoustic wave.

Figure 7:
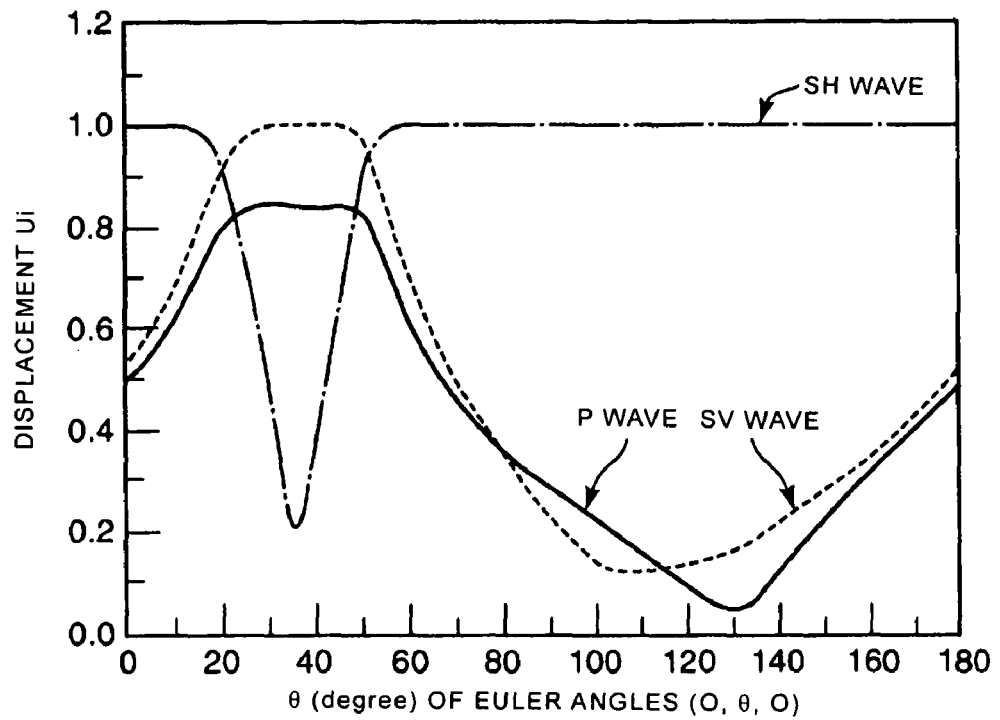
FIG. 7 is a graph showing the displacements U1, U2, and U3 of a P wave, an SH wave, and an SV wave, respectively, propagating on LiTaO$_3$ substrates having Euler angles of which θ is varied.

FIG. 7 is a graph showing the displacement of surface acoustic waves propagating on LiTaO$_3$ substrates having different Euler angles (0°, θ, 0°), θ (degrees) being varied. In this figure, the vertical axis represents the displacement in a normalized form. With reference to FIG. 7, the dotted-chain line indicates the displacement U2 of the SH wave used herein, the solid line indicates the displacement U1 of a P wave, and the broken line indicates the displacement U3 of an SV wave.

As is clear from FIG. 7, when θ of the Euler angles is in the range of about 0° to about 18° or about 58° to about 180°, the displacement U2 of the SH wave is large and constant and the SH wave is principally excited. When the sensor is immersed in liquid as described above, the resonances associated with the Rayleigh wave are weak but the resonances associated with the SH-type surface acoustic wave are not exceedingly weak. Therefore, when the LiTaO$_3$ substrate has Euler angles of which θ is in the range of about 0° to about 18° or about 58° to about 180°, the SH wave can be sufficiently excited if the surface acoustic wave sensors are immersed in liquid.

Furthermore, when θ of the Euler angles is in the range of about 120° to about 140°, the displacement U3 of the resonance associated with the SV wave that is present close to the resonance associated with the SH wave is small. Therefore, θ of the Euler angles is preferably in the range of about 120° to about 140°. This can effectively prevent the deterioration of the frequency response of the surface acoustic wave sensors immersed in liquid because the influence of the SV wave is not large.

Therefore, according to a preferred embodiment of the present invention, the LiTaO$_3$ substrates preferably have Euler angles of which θ is in the range of about 0° to about 18° or about 58° to about 180° and more preferably about 120° to about 140°. This allows the sensors to function well using the SH wave if the sensors are immersed in liquid.

Although it is preferable that θ of the Euler angles is in the range of about 0° to about 18° or about 58° to about 180°, the same advantages as described above can be achieved when the Euler angles are preferably in the range of (0°, 0° to 18°, 0°±5°) or (0°, 58° to 180°, 0°±5°).

EXPERIMENT 2

Figure 8:
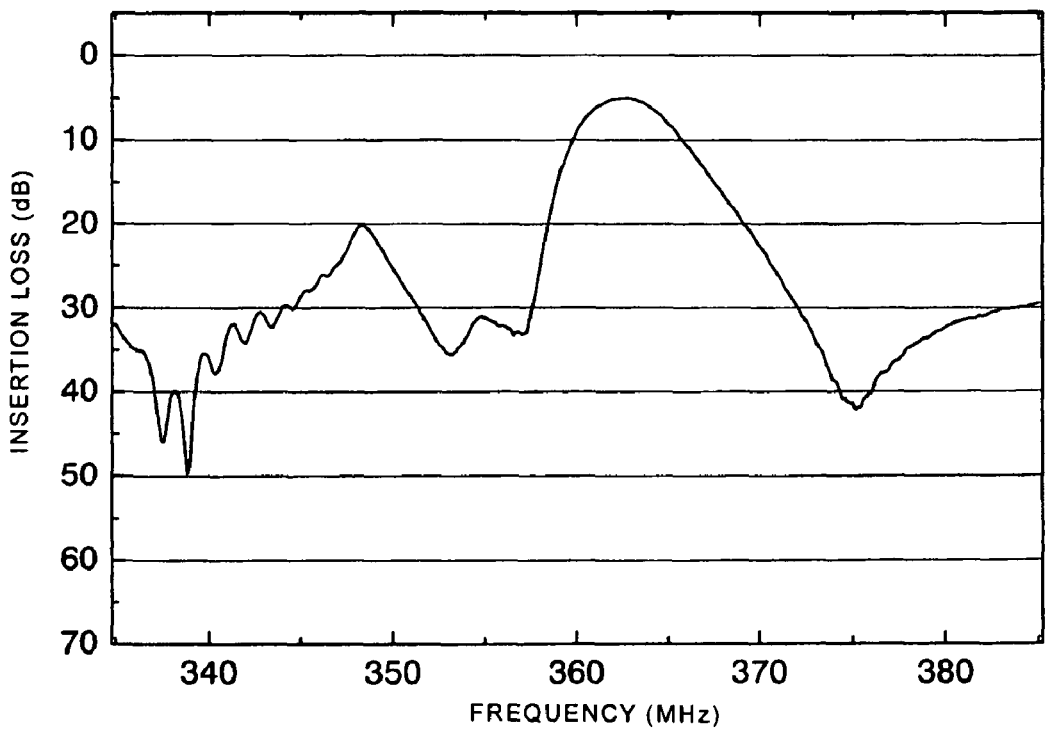
FIG. 8 is a graph showing the relationship between the insertion loss and frequency response of a surface acoustic wave sensor, according to a preferred embodiment of the present invention, including a two-port type surface acoustic wave resonant.

Three types of surface acoustic wave sensors including no reaction membranes were prepared in the same manner as that described in Experiment 1 except that interdigital transducers made of Au had a normalized thickness of about 0.4%, about 2.0%, or about 5.5%. FIG. 8 shows the frequency response of a surface acoustic wave sensor including an interdigital transducer having a normalized thickness of about 2.0%. The three types of surface acoustic wave sensors were immersed in ethanol and alkanethiol was added dropwise to the ethanol such that the concentration thereof was about 140 µmol/l.

The alkanethiol used was 10-carboxy-1-decanethiol-COOH—(CH$_2$)$_{10}$—SH.

The terminal S atom of the alkanethiol reacts with Au contained in the electrodes, whereby a self-assembled monolayer is formed on each Au electrode. The mass of the self-assembled monolayer is applied to the electrode. As a result, the frequency response of the surface acoustic wave sensors is varied as well as that of those surface acoustic wave sensors 1 of the above-described preferred embodiment of the present invention.

Figure 4:
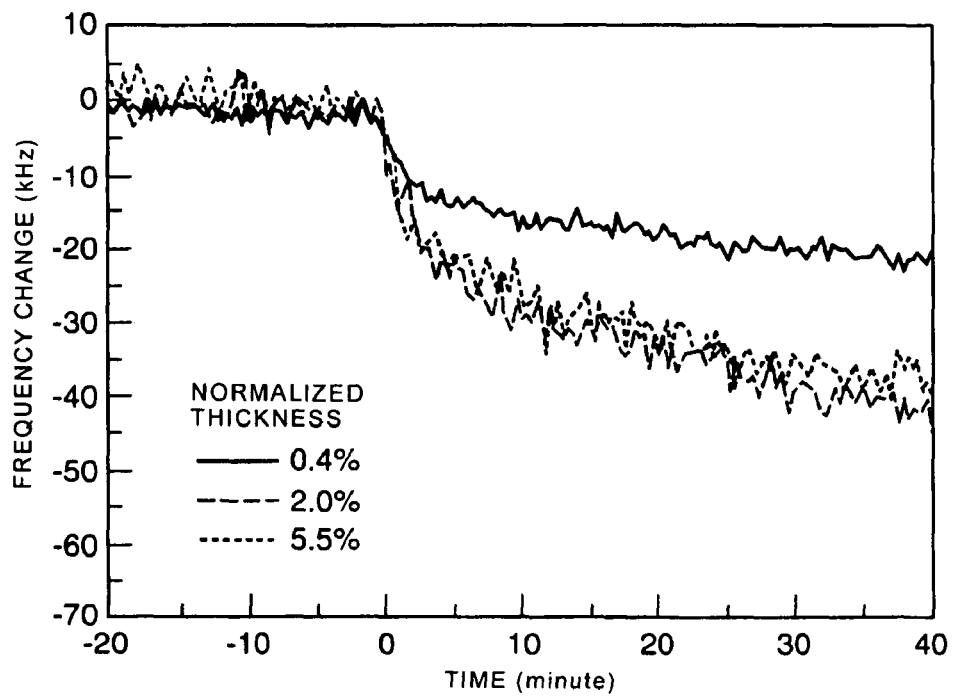
FIG. 4 is a graph showing the time-dependent change in frequency determined by applying a mass to surface acoustic wave elements, prepared in an experiment, including interdigital transducers having different normalized thicknesses.

As a result of the reaction of the alkanethiol with Au contained in the interdigital transducers, the self-assembled monolayers were formed. The frequency response of the surface acoustic wave sensors was varied by the effect of the mass of the self-assembled monolayers. FIG. 4 shows the results. In FIG. 4, the horizontal axis represents the time (minute) elapsed from the dropwise addition of the alkanethiol and the vertical axis represents the change (kHz) in the resonance frequency of an SH-type surface acoustic wave.

As is clear from FIG. 4, for the electrode with a normalized thickness of about 0.4%, the frequency is decreased by about 20 kHz after about 40 minutes elapsed from the dropwise addition of the alkanethiol. On the other hand, for the electrodes with a normalized thickness of about 2.0% or about 5.5%, the frequency is decreased by 40 kHz after about 40 minutes elapsed from the dropwise addition of the alkanethiol. This shows that the variation in the normalized thickness of the electrodes leads to the change in the frequency of the surface acoustic wave sensors.

The self-assembled monolayers made of the alkanethiol are tightly bonded to the interdigital transducers, made of Au, for exciting surface acoustic waves. Therefore, the self-assembled monolayers are preferably used as bonding layers according to a preferred embodiment of the present invention. The use of the self-assembled monolayers effectively enhances the bond between the interdigital transducers and the reaction membranes placed on the bonding layers. This leads to the enhancement in the reliability of the surface acoustic wave sensors. As a result, the change in the mass applied to the reaction membranes can be precisely measured.

A material for forming the bonding layers is not limited to the alkanethiol and any alkanethiol derivative or another compound may be used. Any compound bound to the $LiTaO_3$ substrates and the electrodes for exciting surface acoustic waves can be used.

EXPERIMENT 3

Figure 5:
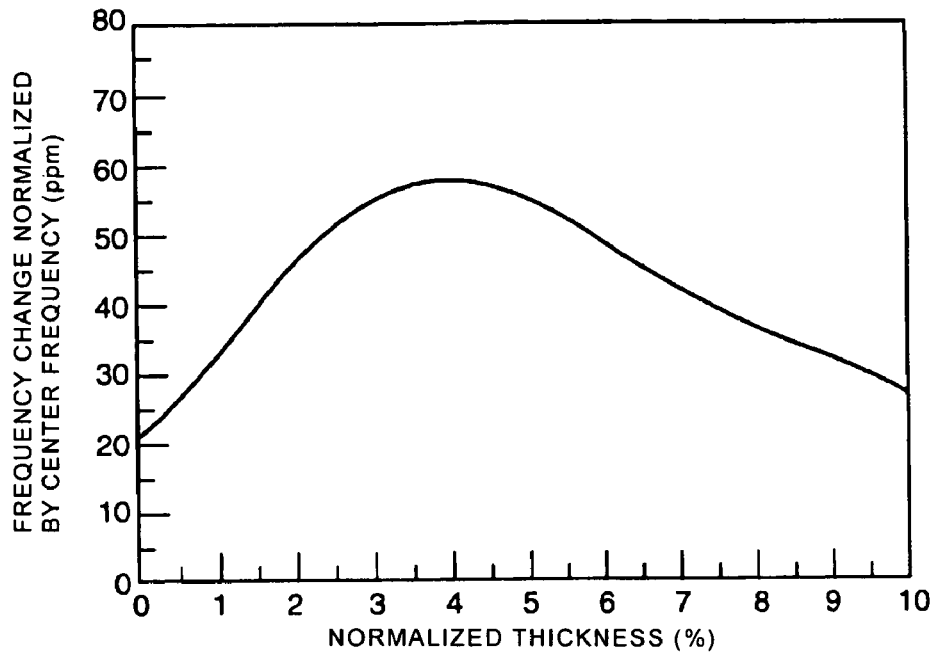
FIG. 5 is a graph showing the change in frequency determined by applying a mass of about 10 ng/mm$^2$ to surface acoustic wave elements, prepared in Experiment 3, including interdigital transducers having different normalized thicknesses.

In consideration of the results of Experiment 2, surface acoustic wave sensors were measured for change in frequency due to the mass of the alkanethiol by varying the normalized thickness of electrodes in the range of about 0% to about 10% in the same manner as that described in Experiment 2. FIG. 5 shows the measurement results.

As is clear from FIG. 5, for the electrodes with a normalized thickness of about 0.8% to about 9.5%, the change in frequency is about 30 ppm or more. A frequency change of about 30 ppm is substantially equal to the change in frequency due to a temperature change of about 0.9° C. Hence, the electrodes with a normalized thickness of about 0.8% to about 9.5% can cope with a temperature change of less than about 0.9° C. In other words, even if the temperature changes by less than about 0.9° C., the change in frequency is greater than the difference in frequency due to the change in temperature. As a result, the change in frequency can be reliably detected.

For the electrodes with a normalized thickness of about 1.2% to about 8.5%, the change in frequency is about 35 ppm or more. The change in temperature that causes a frequency change of about 35 ppm is about 1° C. Therefore, if the electrodes have a normalized thickness of about 1.2% to about 8.5%, the surface acoustic wave sensors can cope with a temperature change of about 1° C.

For the electrodes with a normalized thickness of about 1.9% to about 6.6% or about 3% to about 5%, the change in frequency is about 45 ppm or more or about 55 ppm or more, respectively. The change in temperature that causes a frequency change of about 45 ppm is about 1.3° C. and the change in temperature that causes a frequency change of about 55 ppm is about 1.6° C. When the electrodes have a normalized thickness of about 1.9% to about 6.6% and preferably about 3% to about 5%, the surface acoustic wave sensors including these electrodes can function well even if the temperature changes by about 1.3° C. and about 1.6° C., respectively.

That is, if the change in temperature causes a change in frequency, the surface acoustic wave sensors can function well because these electrodes have a normalized thickness in the above range.

EXPERIMENT 4

Figure 6:
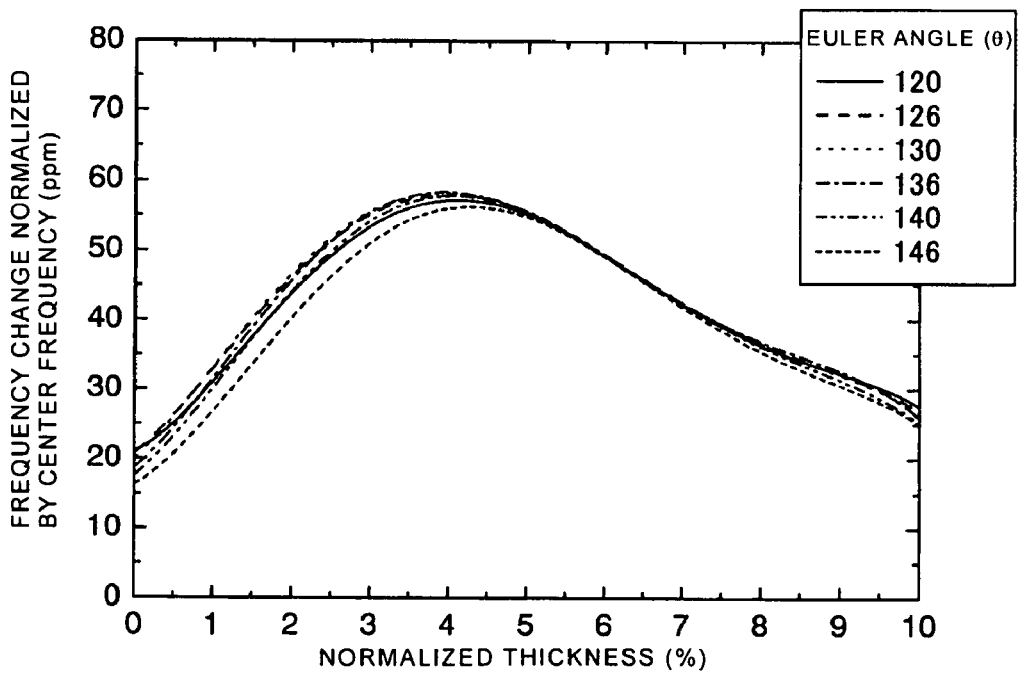
FIG. 6 is a graph showing the relationship between the change in frequency and the normalized thickness of electrodes arranged on LiTaO$_3$ substrates having different Euler angles.

In Experiment 1, the 36°-rotated Y-cut $LiTaO_3$ substrate, that is, the rotated Y-cut $LiTaO_3$ substrate having Euler angles (0°, 126°, 0°) was used. In Experiment 4, $LiTaO_3$ substrates having different Euler angles and normalized thicknesses were prepared and various surface acoustic wave elements including such substrates were prepared. The surface acoustic wave elements were measured for change in frequency due to the mass applied thereto in the same manner as that described in Experiment 1. FIG. 6 shows the measurement results.

The surface acoustic wave elements have substantially the same configuration as that of the surface acoustic wave resonators prepared in Experiment 2 except that the Euler angles of the $LiTaO_3$ substrates were varied.

FIG. 6 shows the displacement of these surface acoustic wave elements including the $LiTaO_3$ substrates in which θ of Euler angles is varied. As is clear from FIG. 6, the variation in Euler angles does not significantly change the relationship between the normalized thickness and the change in frequency. Therefore, the $LiTaO_3$ substrates may have Euler angles sufficient to excite an SH wave.

As is clear from Experiments 1 to 4 described above, when an electrode, principally containing Au, for exciting a surface acoustic wave is placed on a $LiTaO_3$ substrate which have Euler angles (0°, 0° to 18°, 0°±5°) or (0°, 58° to 180°, 0°±5°) and which have a normalized thickness of about 0.8% to about 9.5%, the change in frequency due to the mass applied thereto can be precisely measured using the response of an SH wave. Therefore, according to preferred embodiments of the present invention, a target substance can be precisely detected or determined using a surface acoustic wave element having the above-described configuration and a reaction membrane 4 (see FIG. 1) placed on the surface acoustic wave element.

The reaction membrane is not particularly limited and any reaction membrane suitable to detect a target substance may be used. For example, the following reaction membrane may be used when 2-MIB which is a cause of earthy odor is detected: a reaction membrane containing the camphor-protein complex having a structure similar to that of 2-MIB as disclosed in Japanese Unexamined Patent Application Publication No. 10-90270. Alternatively, when a specific DNA, antigen, or antibody is detected, any reaction membrane containing a substance specifically bound to such a DNA, antigen, or antibody can be used.

The reaction membrane need not necessarily react with a target substance to be bound to the target substance but may react with a bonding substance bound to the target substance.

A specific preferred embodiment of the present invention provides a biosensor in which the reaction membrane contains a substance that can be bound to a biological substance such as a DNA, an antigen, or an antibody and in which the mass applied to a face of a substrate included in a surface acoustic wave sensor is varied due to the bind of the biological substance to the reaction membrane. Therefore, the biological substance can be precisely detected or determined using the biosensor.

Figure 9A:
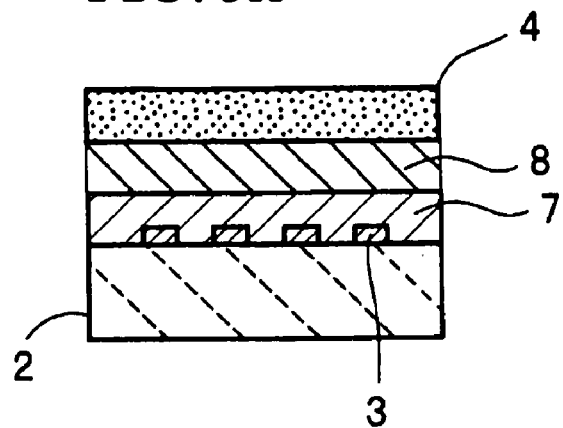
FIGS. 9A and 9B are schematic front sectional views of modifications of a surface acoustic wave sensor, according to a preferred embodiment of the present invention, including a protective layer.

As schematically shown in FIG. 9A, it is preferable that a protective layer 7 cover interdigital transducers 3 arranged on a $LiTaO_3$ substrate 2 and a bonding layer 8 and a reaction membrane 4 be deposited on the protective layer 7 in that order. Since the protective layer 7 is placed between the bonding layer 8 and the interdigital transducers 3, the interdigital transducers 3 and the $LiTaO_3$ substrate 2 can be protected. When the protective layer 7 is made of an insulating material such as $SiO_2$, an undesired short circuit can be prevented from occurring even if a surface acoustic wave sensor is immersed in an electrically conductive liquid. The protective layer 7 also lies over regions outside the interdigital transducers 3. As a result, the bonding layer 8 can be formed over the protective layer 7. This leads to an enhancement in the sensitivity of the sensor.

When the protective layer 7 is made of $SiO_2$ or another material, a material for forming the bonding layer 8 is not an alkanethiol but preferably a methoxysilane such as (CH$_3$O)$_3$SiC$_3$H$_6$OCH$_2$CHCH$_2$O. This is because the methoxy group CH$_3$O is superior in affinity to an inorganic compound such as SiO$_2$.

Figure 9B:
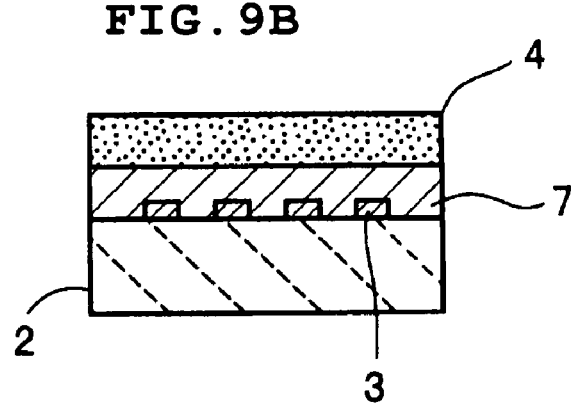

With reference to FIG. 9A, the protective layer 7 is placed between the bonding layer 8 and the interdigital transducers 3. However, as shown in FIG. 9B, a surface acoustic wave device including no bonding layer 8 may include a protective layer 7. In the surface acoustic wave device shown in FIG. 9B, this protective layer 7 is placed between a reaction membrane 4 and interdigital transducers 3. In the device, when this protective layer is made of an insulating material such as SiO$_2$, an undesired short circuit can be prevented from occurring between these interdigital transducers 3. Since this protective layer 7 lies over not only the interdigital transducers 3 but also regions outside the interdigital transducers 3, this reaction membrane 4 can be formed over this protective layer 7. This leads to an enhancement in the sensitivity of the device.

In order to detect a target substance using a surface acoustic wave sensor according to a preferred embodiment of the present invention, a surface acoustic wave device which has substantially the same configuration as that of the surface acoustic wave sensor except that the device includes no reaction membrane may be used as a reference. In this case, the change in frequency due to immersion in liquid can be neglected by determining the difference between the change in frequency due to the immersion of the surface acoustic wave sensor in liquid and the change in frequency due to the immersion of the surface acoustic wave device in liquid. As a result, only the change in frequency due to the bind of the target substance or the bonding substance to a reaction membrane can be precisely measured.

Figure 10:
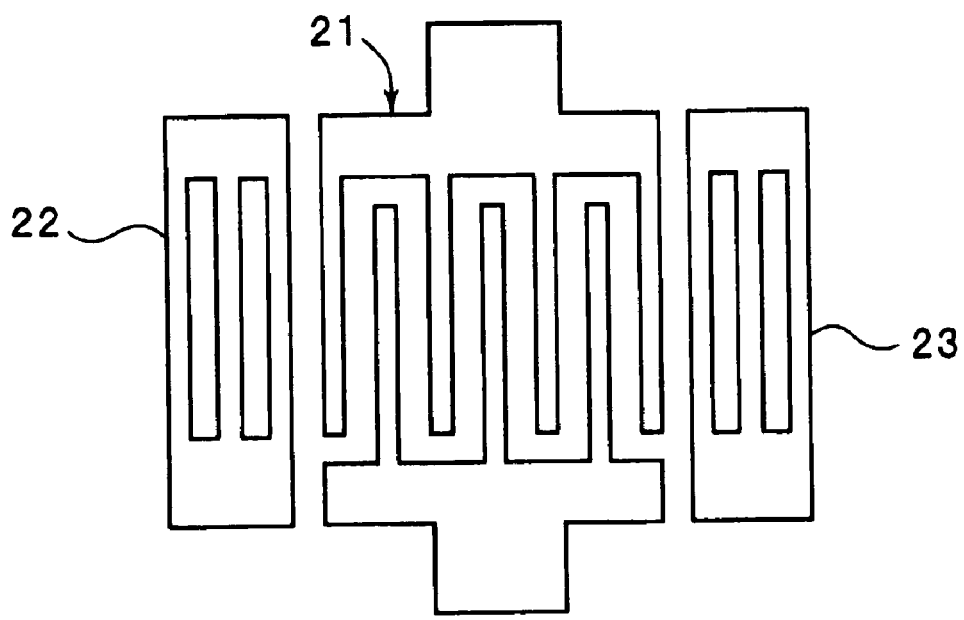
FIG. 10 is a schematic plan view showing the electrode structure of a one-port type surface acoustic wave resonator that is an example of the electrode structure of a surface acoustic wave sensor according to a preferred embodiment of the present invention.
Figure 11:
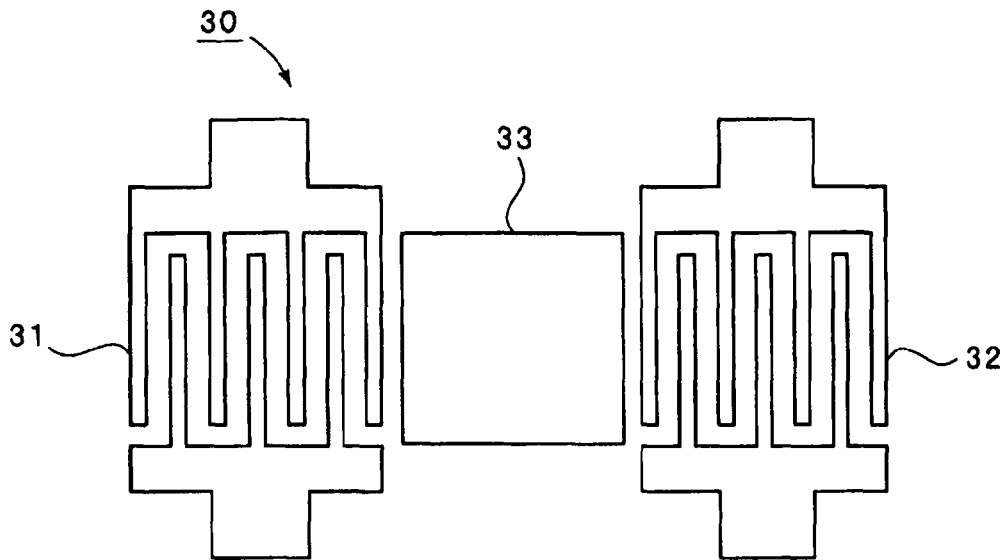
FIG. 11 is a schematic plan view showing the electrode structure of a transversal surface acoustic wave filter that is another example of the electrode structure of a surface acoustic wave sensor according to a preferred embodiment of the present invention.
Figure 12:
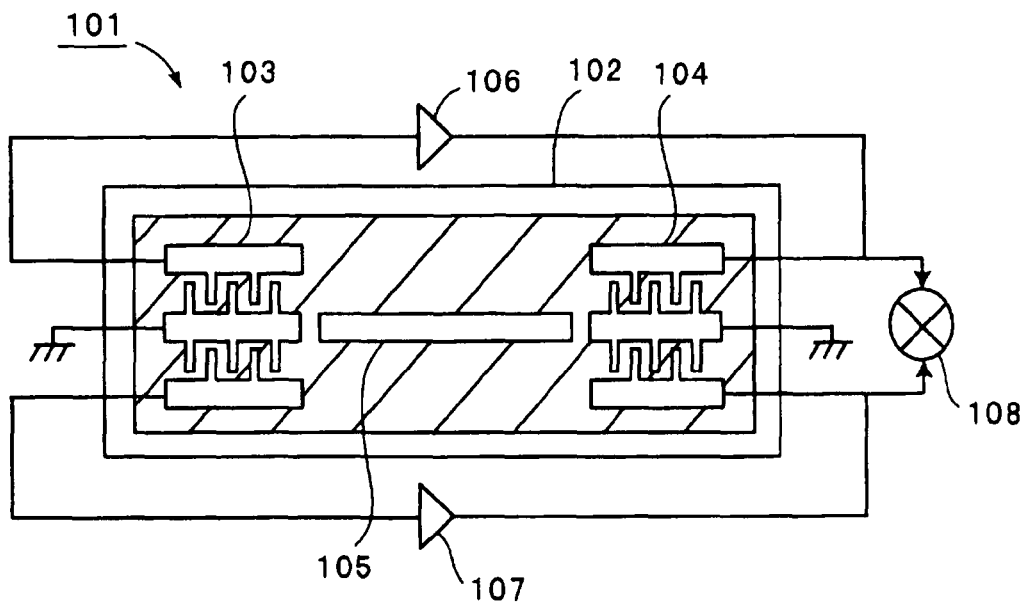
FIG. 12 is a schematic plan view illustrating a known surface acoustic wave sensor.

In the surface acoustic wave sensor, the shape of an electrode, included in a surface acoustic wave element, for exciting a surface acoustic wave is not particularly limited. As shown in FIG. 10, the electrode may be configured such that a one-port type surface acoustic wave resonator including an interdigital transducer 21 and reflectors 22 and 23 can be obtained. Alternatively, as shown in FIG. 11, a transversal surface acoustic wave filter 30 including interdigital transducers 31 and 32 arranged in the direction of the propagation of a surface acoustic wave may be provided. The transversal surface acoustic wave filter 30 may further include a metal thin-film 33 placed between the interdigital transducers 31 and 32 as necessary.

A surface acoustic wave sensor according to various preferred embodiments of the present invention uses an SH-type surface acoustic wave and includes a surface acoustic wave element which includes a rotated Y-cut LiTaO$_3$ substrate having Euler angles (0°, 0° to 15, 0°±5°) or (0°, 58° to 180°, 0°±5°) and which includes electrodes, having a normalized thickness of about 0.8% to about 9.5%, for exciting the surface acoustic wave, the electrodes being arranged on the LiTaO$_3$ substrate, the normalized thickness being determined by normalizing the thickness of the electrodes by the wavelength thereof. Hence, the change in frequency response due to the change in mass applied to the LiTaO$_3$ substrate can be precisely detected. Furthermore, since the surface acoustic wave sensor further includes a reaction membrane covering the electrodes arranged on the LiTaO$_3$ substrate, the change in frequency response can be precisely detected on the basis of the change in mass due to the bind of a target substance to the reaction membrane by reaction or the bind of the binding substance, which is bound to the target substance, to the reaction membrane. Therefore, surface acoustic wave sensors including various reaction membranes suitable for target substances can be greatly enhanced in sensitivity by improving the structure of surface acoustic wave elements.

It has been attempted to enhance the sensitivity of known surface acoustic wave sensors by improving reaction membranes. In preferred embodiments of the present invention, the sensitivity of the surface acoustic wave sensor can be enhanced by improving the structure of the surface acoustic wave element including the reaction membrane.

The electrodes principally contain Au, which hardly reacts with other substances. Hence, the surface acoustic wave sensor hardly becomes dirty and properties thereof hardly deteriorate with time.

When a bonding layer for enhancing the bond between the reaction membrane and the electrodes is placed between the reaction membrane and the electrodes, the surface acoustic wave sensor has high reliability and the mass applied to the reaction membrane can be precisely detected.

Furthermore, when a protective layer made of an insulating material is placed between the electrodes and the reaction membrane or the bonding layer, an undesired short circuit can be prevented from occurring in the surface acoustic wave sensor immersed in a conductive liquid. The protective layer lies over the electrodes and regions outside the electrodes. As a result, the reaction membrane and/or the bonding layer can be formed over the protective layer. This leads to an enhancement in sensitivity.

When the bonding layer is made of alkanethiol, the bonding layer is tightly bonded to the electrodes made of Au, whereby a self-assembled monolayer is formed. Therefore, when the reaction membrane is placed on the bonding layer, the reaction membrane can be tightly bonded to the surface acoustic wave element.

When the electrodes have a normalized thickness of about 1.2% to about 8.5%, preferably about 1.9% to about 6.6%, and more preferably about 3.0% to about 5.0%, the surface acoustic wave sensor has particularly high sensitivity.

Since a biosensor according to the present invention includes the surface acoustic wave device according to a preferred embodiment of the present invention, the reaction membrane contains a substance specifically bound to a biological substance that is a target substance. As a result, the mass applied to the substrate of the surface acoustic wave sensor is varied due to the bind of the biological substance to the reaction membrane. Accordingly, the biological substance can be precisely detected or determined with the biosensor of the present invention.

While the present invention has been described with respect to preferred embodiments thereof, it will be apparent to those skilled in the art that the disclosed invention may be modified in numerous ways and may assume many embodiments other than those specifically set out and described above. Accordingly, it is intended by the appended claims to cover all modifications of the present invention that fall within the true spirit and scope of the invention.

The invention claimed is:

1. A surface acoustic wave sensor for detecting the minute mass applied to a surface acoustic wave element on the basis of the change in frequency using an SH-type surface acoustic wave, the surface acoustic wave sensor comprising:
a rotated Y-cut LiTaO$_3$ substrate having Euler angles of (0°, 120° to 140°, 0°±5°);
electrodes, principally containing Au, and arranged on the LiTaO$_3$ substrate to excite a surface acoustic wave; and
a reaction membrane, bound to a target substance or a binding substance bound to the target substance, covering the electrodes arranged on the LiTaO$_3$ substrate;

wherein the electrodes have a normalized thickness of about 3.0% to about 5.0%, the normalized thickness being determined by normalizing the thickness of the electrodes by the wavelength of the surface acoustic wave;

the surface acoustic wave element is a resonator type surface acoustic wave element; and the electrodes include at least one interdigital electrode and reflectors arranged on both sides of the at least one interdigital transducer in a direction of propagation of a surface acoustic wave.

2. The surface acoustic wave sensor according to claim 1, further comprising a bonding layer, placed between the reaction membrane and the electrodes, and arranged to improve the bond between the reaction membrane and the electrodes.

3. The surface acoustic wave sensor according to claim 1, further comprising a protective layer, placed between the reaction membrane and the electrodes, lying over the electrodes and regions outside the electrodes.

4. The surface acoustic wave sensor according to claim 2, further comprising a protective layer, placed between the bonding layer and the electrodes, lying over the electrodes and regions outside the electrodes.

5. A biosensor comprising the surface acoustic wave sensor according to claim 1, wherein the reaction membrane includes a substance bound to a biological substance that is a target substance and the mass applied to a surface of the substrate of the surface acoustic wave sensor is varied due to the bind of the biological substance to the reaction membrane.

* * * * *